United States Patent [19]

Spiess et al.

[11] Patent Number: 4,816,438

[45] Date of Patent: Mar. 28, 1989

[54] INSULIN-SELECTIVE SOMATOSTATIN ANALOGS

[75] Inventors: Joachim Spiess, Encinitas, Calif.; Bryan D. Noe, Decatur, Ga.

[73] Assignee: The Salk Institute for Biological Studies, San Diego, Calif.

[21] Appl. No.: 33,295

[22] Filed: Apr. 1, 1987

Related U.S. Application Data

[63] Continuation-in-part of Ser. No. 646,610, Aug. 31, 1984, abandoned.

[51] Int. Cl.[4] .................. A61K 37/02; C07K 7/26
[52] U.S. Cl. ...................... 514/11; 530/311; 514/806
[58] Field of Search ............... 514/11, 806; 530/311

[56] References Cited

U.S. PATENT DOCUMENTS

| 4,316,891 | 2/1982 | Guillemin et al. | 514/11 |
| 4,358,439 | 11/1982 | Sieber et al. | 514/11 |
| 4,393,050 | 7/1983 | Vale, Jr. et al. | 514/10 |

OTHER PUBLICATIONS

Nature 288 (1980) 137–141.
J. Biol. Chem. 258 (1982) 1121–1128.

Primary Examiner—Delbert R. Phillips
Attorney, Agent, or Firm—Fitch, Even, Tabin & Flannery

[57] ABSTRACT

Anglerfish somatostatin-28 has the formula:

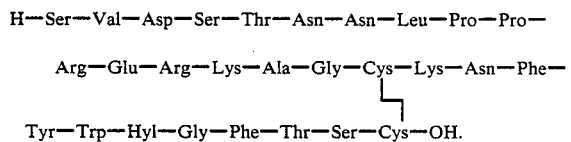

Anglerfish somatostation-28 is insulin-selective when administered in vivo and is useful for the treatment of insulinoma. The 14-residue C-terminal peptide may also be used.

6 Claims, No Drawings

INSULIN-SELECTIVE SOMATOSTATIN ANALOGS

This invention was made with government support under Grant No. DK-26378, awarded by the National Institutes of Health. The Government has certain rights in this invention.

This application is a continuation-in-part of application, Ser. No. 646,610, filed Aug. 31, 1984, now abandoned.

This invention is directed to peptides related to somatostatin and to methods for pharmaceutical treatment of mammals using such peptides. More specifically, the invention relates to 28-residue somatostatin peptides, a 14 residue C-terminal analogue of one of the 28-residue peptides and to pharmaceutical compositions containing such peptides and to methods of treatment of mammals using such peptides.

BACKGROUND OF THE INVENTION

The tetradecapeptide somatostatin-14 was characterized by Guillemin et al. and is described in U.S. Pat. No. 3,904,594 (Sept. 9, 1975.) This tetradecapeptide has the formula:

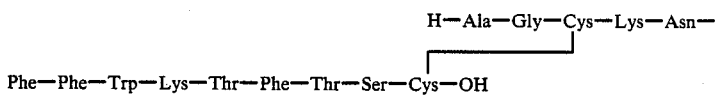

wherein there is a bridging bond between the sulfhydryl groups of the two cysteinyl amino acid residues. The tetradecapeptide in its linear form (sometimes referred to as dihydrosomatostatin), wherein this bridging bond is not present and is replaced by hydrogen, is often considered to be included in the definition "somatostatin" as it appears to have substantially the same biological activity.

Somatostatin-14 and many analogs of somatostatin exhibit activity in respect to the inhibition of growth hormone (GH) secretion from cultured, dispersed rat anterior pituitary cells in vitro and also in vivo and with respect to the inhibition of insulin and glucagon secretion in vivo in the rat and in other mammals. Somatostatin has also been found to inhibit the secretion of gastrin and secretin by acting directly upon the secretory elements of the stomach and pancreas, respectively, and somatostatin is being sold commercially in Europe for the treatment of ulcer patients. The powerful inhibitory effects of somatostatin on the secretion not only of GH but also of insulin and glucagon have led to studies of a possible role of somatostatin in the management or treatment of juvenile diabetes and have proved useful in studying the physiological and pathological effects of these hormones on human metabolism.

L. Pradayrol, et al. in FEBS Letters 109, Jan. 1980, pp 55–58, reported the isolation and characterization of somatostatin-28 (SS-28) from porcine upper small intenstine. Testings of synthetic SS-28 showed increased potency when administered in vivo. SS-28 has the formula:

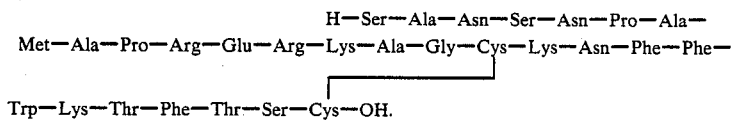

In view of its ability to inhibit the secretion of such hormones, somatostatin may be therapeutically employed in clinical conditions for the treatment of acromegaly, pancreatic islet cell tumors and diabetes mellitus. Because somatostatin has a relatively short duration of action, apparently because it is inactivated by peptidases when administered in vivo, the search has continued for longer-acting somatostatin materials, as well as for somatostatin analogs which are more potent than somatostatin or which are both more potent and exhibit dissociated inhibitory functions.

SUMMARY OF THE INVENTION

A 28-residue peptide having homology with somatostatin-14 has been extracted from anglerfish, purified (i.e. substantially free of related peptides and fragments) and characterized. This peptide is more potent than either somatostatin-14 or somatostatin-28 in inhibiting the secretion of insulin by the pancreas. The 28-member peptide is hereinafter referred to as aSS-28 and has the formula:

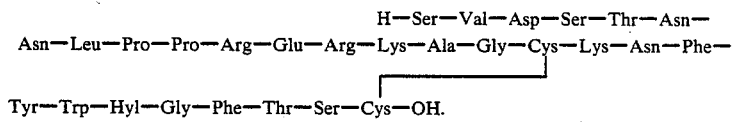

Hyl represents 5-hydroxylysine, which is more specifically referred to as L(2)R-δ-Hydroxylysine, meaning the hydroxyl substitution is on the delta carbon atom. Based upon the biological potency of aSS-28, certain residues may be deleted without adverse effect. The invention also embraces (1) the shorter 14 residues C-terminal analogue of aSS-28 which is hereinafter referred to as aSS-28(15-28)-OH and has the formula:

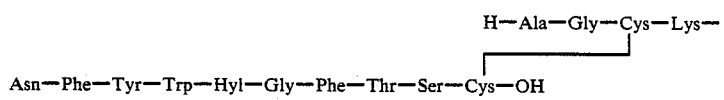

and (2) the 28 residue peptide which is hereinafter referred to as (Lys23)-aSS-28 and has the formula:

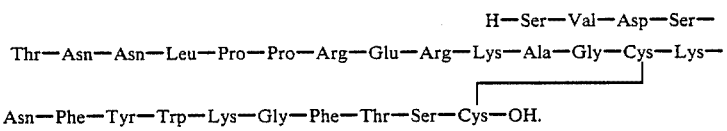

(Lys23)-aSS-28, like aSS-28, has been isolated and characterized from anglerfish pancreatic islets.

Pharmaceutical compositions in accordance with the invention include at least one of the 28-residue peptides and/or the 14 residue peptide or nontoxic addition salt thereof, dispersed in a pharmaceutically acceptable liquid or solid carrier. The administration of such somatostatin analogs or pharmaceutically acceptable addition salts thereof to mammals in accordance with the invention may be carried out for the regulation of secretion of insulin for the treatment of insulinoma.

DETAILED DESCRIPTION OF THE PREFERRED EMBODIMENTS

Somatostatin-28 has been earlier isolated from porcine intestinal extract and from ovine hypothalamic extracts. The nomenclature used to define the peptides is that specified by Schroder and Lubke, "The Peptides", Academic Press (1965) wherein, in accordance with conventional representation, the amino group appears to the left and the carboxyl group to the right. Where the amino acid residue has isomeric forms, it is the L-form of the amino acid that is represented unless otherwise expressly indicated.

The invention provides the 28-residue peptide having the formula:

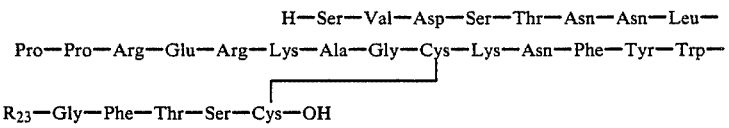

wherein R23 is Hyl or Lys. The invention also provides the 14 residue peptide having the formula

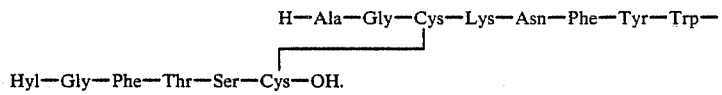

Although not specifically shown herein, the formulas should be understood also to include the linear forms thereof wherein the bridge between the sulfhydryl groups of Cys residues is not present and is replaced by hydrogen.

The peptides may be synthesized by a suitable method, such as by exclusively solid-phase techniques, by partial solid-phase techniques, by fragment condensation, by classical solution addition or by the employment of recently developed recombinant DNA techniques. For example, the techniques of exclusively solid-state synthesis are set forth in the textbook "Solid-Phase Peptide Synthesis", Stewart and Young, Freeman & Co., San Francisco, 1969 and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975). The peptide can be synthesized, if desired, using Lys, which is thereafter converted to Hyl using the enzyme lysine hydroxlase, as described in *Biochemistry*, 11, 122-129 (1972) and *J. Bio. Chem.*, 259, 5403-5 (1984). Production of the synthetic peptides using recombinant DNA techniques will likely be used to satisfy large-scale commercial requirements.

Synthesis by the use of recombinant DNA techniques, for purposes of this application, should be understood to include the suitable employment of a structural gene coding for precursors of aSS-28 and (Lys$^{23}$)-aSS-28. The synthetic aSS-28 and (Lys$^{23}$)-aSS-28 may be obtained by transforming a microorganism using an expression vector including a promoter and operator together with such structural gene and causing such transformed microorganism to express aSS-28 or (Lys$^{23}$)-aSS-28. A non-human animal may also be used to produce aSS-28 or (Lys$^{23}$)-aSS-28 by gene-farming using such a structural gene and the general techniques set forth in U.S. Pat. No. 4,276,282 issued June 30, 1981 or using microinjection of embryos as described in WO83/01783 published May 26, 1983 and WO82/04443 published Dec. 23, 1982.

Common to coupling-type syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues linked to the side-action protecting groups.

Also considered to be within the scope of the present invention are the intermediates of the formulae:

$X^1$—Ser($X^2$)—Val—Asp($X^5$)—Ser($X^2$)—Thr($X^8$)—
Asn($X^3$)—Asn($X^3$)—Leu—Pro—Pro—Arg($X^4$)—Glu($X^5$)—
Arg($X^4$)—Lys($X^6$)—Ala—Gly—Cys($X^7$)—Lys($X^6$)—Asn($X^3$)—
Phe—Tyr($X^9$)—Trp—Hyl($X^2$)($X^6$)—Gly—Phe—Thr($X^8$)—

-continued

Ser($X^2$)—Cys($X^7$)—$X^{10}$, $X^1$—Ser($X^2$)—Val—Asp($X^5$)—Ser($X^2$)—Thr($X^8$)—Asn($X^3$)—Asn($X^3$)—Leu—Pro—Pro—Arg($X^4$)—Glu($X^5$)—Arg($X^4$)—Lys($X^6$)—Ala—Gly—Cys($X^7$)—Lys($X^6$)—Asn($X^3$)—Phe—Tyr($X^9$)—Trp—Lys($X^6$)—Gly—Phe—Thr($X^8$)—Ser($X^2$)—Cys($X^7$)—$X^{10}$, and $X^1$—Ala—Gly—Cys($X^7$)—Lys($X^6$)—Asn($X^3$)—Phe—Tyr($X^9$)—Trp—Hyl($X^2$)($X^6$)—Gly—Phe—Thr($X^8$)—Ser($X^2$)—Cys($X^7$)—$X^{10}$ wherein $X^1$ is either hydrogen or an a-amino protecting group. The a-amino protecting groups contemplated by $X^1$ are those known to be useful in the art in the stepwise synthesis of polypeptides. Among the classes of a-amino protecting groups covered by $X^1$ are (1) acyl-type protecting groups, such as formyl, trifluoroacetyl, phthalyl, p-toluenesulfonyl(Tos), benzensulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl(trityl), benzyl(Bzl); (7) trialkylsilane groups, such as trimethylsilane. The preferred α-amino protecting group is BOC.

$X^2$ and $X^8$ are protecting groups for a side-chain hydroxyl group of Thr and Ser, respectively, and are preferably selected from the class consisting of acetyl-(Ac), benzoyl(Bz), tert-butyl, trityl, tetrahydropyranyl, benzyl ether(Bzl), 2,6-dichlorobenzyl and Z. The most preferred protecting group is Bzl. $X^2$ and/or $X^8$ can be hydrogen, which means there is no protecting group on the hydroxyl group.

$X^3$ is hydrogen or a protecting group for the amido group of Asn and is preferably xanthyl(Xan).

$X^4$ is a protecting group for the guanidino group of Arg preferably selected from the class consisting of nitro, Tos, Z, adamantyloxycarbonyl and BOC, or is hydrogen. Tos is most preferred.

$X^5$ is hydrogen or an ester-forming protecting group for the carboxyl group of Asp or Glu preferably selected from the class consisting of Bzl, 2,6-dichlorobenzyl(DCB), CBZ, methyl and ethyl. OBzl is most preferred.

$X^6$ is hydrogen or a protecting group for the side chain amino substituent of Lys. Illustrative of suitable side chain amino protecting groups are Z, 2-chlorobenzyloxycarbonyl(2-Cl-Z), Tos, t-amyloxycarbonyl and BOC. The selection of a side chain amino protecting group is not critical except that it must be one which is not removed during deprotection of the a-amino groups during the synthesis. Hence, the a-amino protecting group and the side chain amino protecting group cannot be the same.

$X^7$ is a protecting group for Cys preferably selected from the class consisting of p-methoxybenzyl(MeOBzl), p-methylbenzyl, acetamidomethyl, trityl and Bzl. The most preferred protecting group is p-methoxybenzyl.

$X^7$ can also be hydrogen, meaning that there is no protecting group on the sulfur.

$X^9$ is a protecting group for the hydroxyl group of Tyr preferably selected from the class consisting of 2,6-dichlorobenzyl(DCB), Bzl, MeOBzl and OBzl. The most preferred is DCB.

$X^{10}$ is selected from the class consisting of OH, $OCH_3$, amides, hydrazides and esters, including a benzyl ester or a hydroxymethyl ester anchoring bond used in solid phase synthesis for linking to a solid resin support, represented by the formulae:

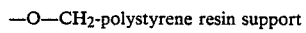

and

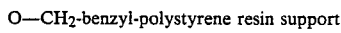

The polystyrene polymer is preferably a copolymer of styrene with about 0.5 to 2% divinyl benzene as a cross-linking agent, which causes the polystyrene polymer to be completely insoluble in certain organic solvents.

In the formula for the intermediate, at least one of $X^1$, $X^2$, $X^3$, $X^4$, $X^5$, $X^6$, $X^7$, $X^8$ and $X^9$ is a protecting group. In selecting a particular side chain protecting group to be used in the synthesis of the peptides, the following rules are followed: (a) the protecting group should be stable to the reagent and under the reaction conditions selected for removing the alpha -amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching α-amino- and S-protected Cys to a chloromethylated resin or to a hydroxymethyl resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6.

Cys protected by BOC and by p-methoxybenzyl is coupled to the chloromethylated polystyrene resin according to the procedure of Monahan and Gilon, *Biopolymer* 12, pp 2513-19, 1973. Following the coupling of BOC-(p-methoxybenzyl)(Cys) to the resin support, the α-amino protecting group is removed, as by using trifluoroacetic acid (TFA) in methylene chloride, TFA alone or with HCl in dioxane. Preferably 50 weight % TFA in methylene chloride is used with 0-5 weight % 1,2 ethane dithiol. The deprotection is carried out at a temperature between about 0° C. and room temperature. Other standard cleaving reagents and conditions for removal of specific α-amino protecting groups may be used as described in Schroder and Lubke, "The Peptides", 1 pp 72-75 (Academic Press 1965).

After removal of the α-amino protecting group of Cys, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are: (1) carbodiimides, such as N,N'-diisopropyl carbodiimide, N-ethyl-N'-(3-dimethylaminopropyl)carbodiimide; (2) cyanamides such as N,N'-dibenzylcyanamide; (3) keteimines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) nitrogen-containing heterocyclic compounds having a hydroxy group on one ring nitrogen, such as N-hydroxyphthalimide, N-hydroxysuccinimide and 1-hydroxybenzotriazole(HOBT). Other activating reagents and their use in peptide coupling are described by Schroder and Lubke, supra, in Chapter III and by Kapoor, *J. Phar. Sci.*, 59, pp 1-27 (1970).

Each protected amino acid or amino acid sequence is introduced into the solid phase reactor in about a fourfold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the a-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp.1927-1938, or as reported in Gray et al. *Biochemistry* Vol. 23, 12, pp 2796-2802 (1984).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X_2$, $X_3$, $X_4$, $X_5$, $X_6$, $X_7$, $X_8$ and $X_9$ and the α-amino protecting group $X_1$, to obtain the peptide in its linear form. If the synthesis was carried out using Lys and the Hyl-containing peptide is desired, the linear peptide is now treated with lyside hydroxylase. The cyclic form of the peptide is obtained by oxidizing using a ferricyanide solution, preferably as described in Rivier et al., *Biopolymers*, Vol. 17 (1978), 1927-38, or by air oxidation, or in accordance with other known procedures.

As an alternative route, the intermediate peptide may be separated from the resin support by alcoholysis after which the recovered C-terminal ester is converted to the acid by hydrolysis. Any side chain protecting groups may then be cleaved as previously described or by other known procedures, such as catalytic reduction (e.g. Pd on $BaSO_4$) using conditions which will keep the Trp moiety intact. When using hydrogen fluoride for cleaving, anisole and methylethyl sulfide are included in the reaction vessel for scavenging. When Met is present in the sequence, the BOC protecting group is cleared with trifluoroacetic acid(TFA)/ethane-dithiol prior to cleaving from the resin to eliminate S-alkylation; and furthermore, cleavage from the resin is carried out in the presence of methyl ethyl sulfide as a scavenger.

The following Examples set forth the preferred methods for synthesizing aSS-28 and analogs by the solid-phase technique.

EXAMPLE I

The synthesis of aSS-28 having the formula:

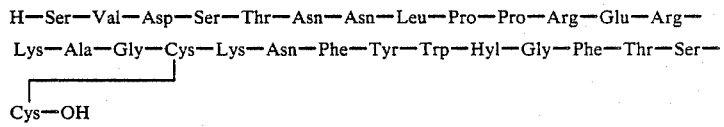

is conducted in a stepwise manner on a chloromethylated resin, such as LS-601 available from Lab Systems, Inc., containing 0.9 Meq Cl/gm. resin. Coupling of BOC-(p-methoxybenzyl) Cys to the resin is performed by the procedure set forth by Horiki et al., in *Chemistry Letters* (Chem. Soc. of Japan) (1978) pp. 165-168, and it results in the substitution of about 0.35 mmol. Cys per gram of resin. The amino acid 5-hydroxylysine is synthesized by the procedure set forth by Izumiya et al., in *Bull. Chem. Soc. Japan,* 35, 2006 (1962). Separation of the D and L isomers is accomplished by the procedure of Keoners et al. in *Tetrahedron,* Vol. 37, 1763-1771 (1981). All solvents that are used are carefully degassed, preferably by sparging with an inert gas, e.g. helium, to insure the absence of oxygen that might undesirably oxidize the sulfur of the Met residue or the Trp.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Trp or BOC-Arg(Tos) or BOC-Asn(Xan) is being coupled, a mixture of 10% DMF and methylene chloride is used. Bzl is used as the hydroxyl side-chain protecting group for Ser and Thr also for the OH-group on Hyl. BOC-Asn is coupled overnight using one equivalent of HOBt in a 50% mixture of DMF and methylene chloride. 2-Cl-Z is used as the protecting group for the amino group of the side chain on Lys and Hyl, and DCB is used to protect Tyr. Tos is used to protect the guanidino group of Arg, and the glutamic and aspartic carboxyl groups are protected by OBzl. The amido group of Asn is protected by Xan. At the end of the synthesis, the following composition is obtained BOC-Ser(Bzl)-Val-Asp(OBzl)-Ser(Bzl)-Thr(Bzl)-Asn(Xan)-Asn(Xan)-Leu-Pro-Pro-Arg(Tos)-Glu(OBzl)-Arg(Tos)-Lys(2-Cl-Z)-Ala-Gly-Cys(MeOBzl)-Lys(2-Cl-Z)-Asn(Xan)-Phe-Tyr(DCB)-Trp-Hyl(Bzl)(2-Cl-Z)-Gly-Phe-Thr(Bzl)-Ser(Bzl)-Cys(MeOBzl)-O-CH₂-benzene-polystyrene resin support.

In order to cleave and deprotect the resulting protected peptide-resin, it is treated with 1.5 ml. anisole, and 15 ml. hydrogen fluoride (HF) per gram of peptide-resin, first at −20° C. for 20 min. and then at 0.° C. for one-half hour. After elimination of the HF under high vacuum, the resin-peptide is washed alternately with dry diethyl ether and chloroform, and the peptides are then extracted with de-gassed 2N aqueous acetic acid and separated from the resin by filtration.

The cleaved and deprotected peptide is then and added dropwise to a potassium ferricyanide solution to form the disulfide bond between the Cys residues, as described by Rivier et al. in Biopolymers, Volume 17 (1978) pp. 1927–1938. After cyclization, the peptide is chromatographed on both anion- and cation-exchange resins using the methods described in the Rivier et al. article and then lyophilized.

The peptide is then purified by gel permeation followed by semi-preparative HPLC as described in Rivier et al., *Peptides: Structure and Biological Function* (1979) pp. 125–128 and in J. Rivier et al. *J. Chromatography*, 288 (1984) P. 303–328. The chromatographic fractions are carefully monitored by HPLC, and only the fractions showing substantial purity were pooled.

To check whether the precise sequence was achieved, some purified aSS-28 is hydrolyzed in sealed evacuated tubes containing 4N methanesulfonic acid and 0.2% tryptamine for 24 hours at 110° C. Amino acid analyses of the hydrolysates using a Beckman 121 MB amino acid analyzer shows that the 28-residue peptide structure was obtained.

EXAMPLE II

The synthesis of aSS-28 having the formula:

protecting group for the amino group of the side chain on Lys, and DCB is used to protect Tyr. The guanidino group of Arg is protected by Tos, and OBzl is used to protect the glutamic and aspartic carboxyl groups. The Amido group of Asn is protected by Xan. The following composition is obtained upon completion of the synthesis: BOC-Ser(Bzl)-Val-Asp(OBzl)-Ser(Bzl)-Thr(Bzl)-Asn(Xan)-Asn(Xan)-Leu-Pro-Pro-Arg(Tos)-Glu(OBzl)-Arg(Tos)-Lys(2-Cl-Z)-Ala-Gly-Cys(MeOBzl)-Lys(2-Cl-Z)-Asn(Xan)-Phe-Tyr(DCB-Trp-Lys( 2-Cl-Z)-Gly-Phe-Thr(Bzl)-Ser(Bzl)-Cys(MeOBzl)-O-CH₂-benzene-polystyrene resin support.

After the desired amino-acid sequence has been completed, the resulting intermediate peptide is treated with 1.5 ml. anisole and 15 ml. (HF) per gram of peptide resin, first at −20° C. for 20 minutes and then at 0° C. for one-half hour in order to cleave and deprotect the peptide. The resulting cleaved and deprotected peptide is now in its linear form. After elimination of the HF under high vacuum, the resin-peptide is washed alternatively with dry diethyl ether and chloroform, and the peptides are then extracted with de-gassed 2N aqueous acetic acid and separated from the resin by filtration.

The lysine residue nearest the c-terminus of the peptide is then converted to hydroxylysine by treating the entire peptide chain with the enzyme protocollagen lysine hydroxylase. Although the peptide possesses two other lysine residues, only the third lysine residue of the peptide, at position 23 in the amino-acid chain, is converted to hydroxylysine by treating the peptide chain with the enzyme. A critical determinant for the hydroxylation of lysine in a peptide linkage upon treatment with lysine hydroxylase is that the lysine residue be in a position immediately preceding glycine. Since the first two lysine residues in the peptide chain, at positions 14 and 18, do not meet this requirement, they will not be converted to hydroxylysine, whereas the third lysine residue, which is immediately followed by glycine, will be converted to hydroxylysine upon treatment with the enzyme.

The reaction of the peptide with lysine hydroxylase under standard conditions is carried out in a final volume of 1.0 ml. containing 40–60 μg of enzyme prepara-

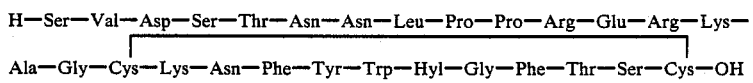

H—Ser—Val—Asp—Ser—Thr—Asn—Asn—Leu—Pro—Pro—Arg—Glu—Arg—Lys—
Ala—Gly—Cys—Lys—Asn—Phe—Tyr—Trp—Hyl—Gly—Phe—Thr—Ser—Cys—OH is conducted in a step-by-step fashion on a chloromethylated resin containing 0.9Meg Cl/gm resin, such as LS-601, available from Lab Systems, Inc. BOC-(p-methoxybenzyl) Cys is coupled to the resin by the procedure set forth by Horiki et al., in *Chemistry Letters* (Chem. Soc. of Japan) (1978) pp. 165–168, which results in the substitution of about 0.35 mmol. Cys per gram of resin.

The peptide chain is built step-by-step on the resin after deprotection and neutralization. In general, 1 to 2 mmol. of BOC-protective amino acid and methylene chloride is used per gram of resin, plus one equivalent of 2 molar DCCI methylene chloride, for two hours. When BOC-Trp or BOC-Arg (Tos) or BOC-Asn (Xan) is being coupled to the residue, a mixture of 10% DMF and methylene chloride is used. Bzl is used as the hydroxyl side-chain protecting group for Ser. and Thr. BOC-Asn is coupled overnight using one equivalent of HOBt in a 50% mixture of DMF and methylene chloride. 2-chlorobenzyloxycarbonyl (2-Cl-Z) is used as the tion, 0.05 mM FeSO₄, 0.1 mM alpha-ketoglutarate (60,000 dpm), 0.5 mM ascorbic acid, 0.1 mg of catalase (Calbiochem), 0.1 mM dithiothreitol (Calbiochem), 2 mg of bovine serum albumin (Sigma), and 50 mM Tris-HCl buffer adjusted to pH 7.8 at 25 ° C. (Kivirikko and Prockop, 1972). The peptide is heated to 100° C. for 10 min. and cooled to 0° C. just before addition to the incubation system. The samples are incubated at 37° C. for 40 minutes. The reaction is terminated by injecting 1 ml of 1 M potassium phosphate (pH 5.0).

The cleaved and deprotected peptide is then added dropwise to a potassium ferrous cyanide solution to form the disulfide bond between the Cys residues, as described in Rivier et al., *Biopolymers,* Vol. 17, (1978), pp. 1927–1938. After the cyclic form of the peptide is obtained, the peptide is chromatographed on both anion- and cation-exchange resins using the procedure described in the Rivier et al. article and then lyophilized.

The peptide is then purified by gel permeation followed by semi-preparative HPLC as described in River et al., *Peptides: Structure and Biological Function* (1979) pp. 125–128 and in J. Rivier et al., *J. Chromatography,* 288 (1984) pp. 303–328. The chromatographic fractions are carefully monitored by HPLC, and only the fractions showing substantial purity were pooled.

To ascertain whether the precise amino acid sequence was obtained, some purified aSS-28 is hydrolyzed in sealed evacuated tubes containing 4N methanesulfonic acid and 0.2% tryptamine for 24 hours at 110° C. Amino acid analysis of the hydrolysates using a Beckman 121 MB amino acid analyzer and automated Edman degradation on an Applied Biosystems 470A Protein Sequencer (equipped with an Applied Biosystems 120A-PHT Analyzer and a Hewlett-Packard 3393A Integrator) demonstrate that the 28-residue peptide structure was achieved.

EXAMPLE III

The synthesis described in Example I is repeated using BOC-Lys(2-Cl-Z) instead of BOC-Hyl(Bzl) (2-Cl-Z) for the residue in the 23-position in order to prepare [Lys$^{23}$]-aSS-28. After linking the first 14 residues to the resin, a portion of the peptido-resin is removed and is hereafter used to produce the 14-residue peptide. After the entire 28-residue sequence is completed, it is cleaved and deprotected in the same manner as in Example I. The 14-residue peptidoresin is similarly treated. The cleaved and deprotected peptides are then extracted and separated from the resin; then they are purified as taught in Example I. A portion of the 28-residue peptide is removed to facilitate its testing for biological potency following cyclization.

The remainder of the 28-residue peptide is then treated with lysine hydroxylase to convert the [Lys$^{23}$]-aSS-28 to aSS-28. Chick embryos are homogenized, and lysine hydroxylase is purified from the supernatant using procedures well known in the art. A reaction mixture is then prepared containing about 50 micrograms of the enzyme, 0.05 mM FeSo$_4$, 0.1 mM a-ketoglutarate, 0.5 mM ascorbic acid, 0.1 mg of catalase (CalBiochem), 0.1 mM dithiothreitol (CalBiochem), 2 mg of bovine serum albumin (Sigma) and 50 mM Tris-HCl buffer adjusted to pH 7.8 at about 25° C. The purified 28-residue peptide is added and then incubated at about 37° C. for about 80 minutes.

The peptide is extracted using dialysis at about 4° C. for about 16 hours against several changes of 0.02M ammonium bicarbonate (pH 7.6), containing 0.01 mM calcium chloride. The solution carrying the peptide is then evaporated to dryness, and the residue is then subjected to cyclization and HPLC purification as in Example I. A sample is removed and tested by amino acid analysis, which indicates the presence of one residue of hydroxylysine and two residues of lysine. It is known that the enzyme will selectively hydroxylate a lysine residue which is connected to a glycine residue at its C-terminus; accordingly, the other lysine residues present in the 14-and 18-positions are not hydroxylated.

The 14-residue peptide is similarly treated with lysine hydroxylase to convert it to aSS(15–28).

To determine the effectiveness of the peptides to inhibit the release of insulin, in vitro radioimmunoassays are carried out using aSS-28, [Lys$^{23}$]-aSS-28 and aSS(15-28) in side-by-side comparison with equimolar concentrations of somotostatin-14 having a known effectiveness to inhibit the release of growth hormone induced by the application of isobutyl methyl xanthine to pituitary cells. Cultures are used which include cells of rat pituitary glands removed some four to five days previously in a system that minimizes enzymatic degradation, generally following the procedure set forth in Vale et al., *Methods in Enzymology, Hormones and Cyclic Nucleotides* (1975) Vol. 37, p. 82. Both cultures of a defined standard medium and cultures which are considered optimal for the secretion of growth hormone, as a result of having additions of either 2% or 10% of serum from a foetal calf, are used for the comparative testing. The results of this comparative testing show that aSS-28 is likely insulin-selective because its inhibition of GH is substantially less than SS-14. aSS(15–28) and [Lys$^{23}$]-aSS-28 are similarly biologically active although having somewhat lower potencies.

In vivo experiments are carried out with aSS-28, using the procedure described in Brown et al., *Metabolism* (1976) Vol. 25, pp. 1501–1503, to determine the potency, relative to somatostatin-14, to inhibit the secretion of glucagon and insulin stimulated by the administration of arginine to groups of rats.

aSS-28 exhibits increased potency to inhibit basal and stimulated insulin secretion in mammals, including humans and dogs, and is believed to have a direct effect upon the pancreatic cells to selectively inhibit insulin release. Accordingly, the administration to mammals of an effective amount of aSS-28 (or a non-toxic, pharmaceutically acceptable addition salt thereof) can be used to inhibit the release of insulin in mammals and may be employed in the treatment of insulinoma, under the guidance of a physician. It is expected that aSS-28 will also decrease gastric acid secretion and influence thermoregulation.

Because aSS-28 exhibits such an extreme insulin-selectivity, this peptide may be particularly valuable for the treatment of insulinoma which would otherwise result in the secretion of large quantities of insulin and resultant hypoglycemia.

The peptides of the invention or the nontoxic addition salts thereof, combined with a pharmaceutically acceptable carrier to form a pharmaceutical composition, may be administered to mammals, including humans, either intravenously, subcutaneously, intramuscularly, intranasally or orally. The administration may be employed by a physician to inhibit the release of insulin. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain at least one of the peptides in conjunction with a conventional, pharmaceutically-acceptable carrier. Usually, the dosage will be from about 2 to about 200 micrograms of the peptide per kilogram of the body weight of the host. Overall, treatment of subjects with these peptides is generally carried out in the same manner as the treatment using somatostatin itself.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the somatostatin peptide chain can be made in accordance with present or future developments without detracting from the potency of the analogs, particularly deletions may be made to create shortened fragments having substantial biological potency, and such peptides are considered as being within the scope of the invention. As earlier indicated, the linear form as well as the preferred cyclic form is considered to be within the scope of the invention.

Various features of the invention are emphasized in the claims which follow.

What is claimed is:

1. A pharmaceutical composition for the treatment of insulinoma comprising an effective amount of a compound selected from the group consisting of H—Ser—Val—Asp—Ser—Thr—Asn—Asn—Leu—Pro—Pro—
Arg—Glu—Arg—Lys—Ala—Gly—Cys—Lys—Asn—Phe—
Tyr—Trp—Hyl—Gly—Phe—Thr—Ser—Cys—OH and H—Ala—Gly—Cys—Lys—Asn—Phe—Tyr—Trp—Hyl—
Gly—Phe—Thr—Ser—Cys—OH, or a nontoxic addition salt of either, plus a pharmaceutically acceptable liquid or solid carrier therefor.

2. A pharmaceutical composition in accordance with claim 1 wherein said compound has the formula:

H—Ser—Val—Asp—Ser—Thr—Asn—Asn—Leu—Pro—Pro—
Arg—Glu—Arg—Lys—Ala—Gly—Cys—Lys—Asn—Phe—
Tyr—Trp—Hyl—Gly—Phe—Thr—Ser—Cys—OH.

3. A compound selected from the group consisting of

H—Ser—Val—Asp—Ser—Thr—Asn—Asn—Leu—Pro—Pro—
Arg—Glu—Arg—Lys—Ala—Gly—Cys—Lys—Asn—Phe—
Tyr—Trp—Hyl—Gly—Phe—Thr—Ser—Cys—OH, the linear version thereof where the disulfide bridge is replaced by hydrogen, H—Ala—Gly—Cys—Lys—Asn—Phe—Tyr—Trp—Hyl—
Gly—Phe—Thr—Ser—Cys—OH, and the linear version thereof where the disulfide bridge is replaced by hydrogen.

4. A compound in accordance with claim 3 having the formula:

H—Ser—Val—Asp—Ser—Thr—Asn—Asn—Leu—Pro—Pro—
Arg—Glu—Arg—Lys—Ala—Gly—Cys—Lys—Asn—Phe—
Tyr—Trp—Hyl—Gly—Phe—Thr—Ser—Cys—OH.

5. A method of treating insulinoma comprising administering an effective amount of a compound selected from the group consisting of H—Ser—Val—Asp—Ser—Thr—Asn—Asn—Leu—Pro—Pro—
Arg—Glu—Arg—Lys—Ala—Gly—Cys—Lys—Asn—Phe—
Tyr—Trp—Hyl—Gly—Phe—Thr—Ser—Cys—OH;

H—Ala—Gly—Cys—Lys—Asn—Phe—Tyr—Trp—Hyl—
Gly—Phe—Thr—Ser—Cys—OH;

and the nontoxic addition salts of either.

6. A method of treatment in accordance with claim 5 wherein said compound has the formula H—Ser—Val—Asp—Ser—Thr—Asn—Asn—Leu—Pro—Pro—Arg—Glu—Arg—Lys—Ala—Gly—Cys—Lys—Asn—Phe—Tyr—Trp—Hyl—Gly—Phe—Thr—Ser—Cys—OH.

* * * * *

UNITED STATES PATENT AND TRADEMARK OFFICE
CERTIFICATE OF CORRECTION

PATENT NO. : 4,816,438
DATED : March 28, 1989
INVENTOR(S) : Joachim Spiess et al.

It is certified that error appears in the above-identified patent and that said Letters Patent is hereby corrected as shown below:

Column 3, line 2, change "(Lys 23)" to --(Lys$^{23}$)--.

Column 3, line 10, change "(Lys 23)" to --(Lys$^{23}$)--.

Column 3, line 44, change "R23" to --R$_{23}$--.

Column 8, line 3, change "lyside" to --lysine--.

Column 9, line 65, change "Ser." to --Ser--.

Column 10, line 9, delete the "-" (hyphen) at the end of "Cys(-".

Column 10, line 12, delete the "-" (hyphen) at the end of "Cys(-".

Column 11, line 41, change "FeSo$_4$" to --FeSO$_4$--.

Signed and Sealed this

Ninth Day of January, 1990

Attest:

JEFFREY M. SAMUELS

Attesting Officer    Acting Commissioner of Patents and Trademarks